(12) United States Patent
Vatter et al.

(10) Patent No.: US 6,224,888 B1
(45) Date of Patent: May 1, 2001

(54) COSMETIC COMPOSITIONS

(75) Inventors: Michael Lee Vatter, Okeana; David Edmund Tarantino, Loveland, both of OH (US); Nichole Marie Scherneck, Baltimore; Michael Gary Armstrong, Jr., Randallstown, both of MD (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/249,217

(22) Filed: Feb. 12, 1999

(51) Int. Cl.$^7$ .............................. A61K 6/00; A61K 7/00; A61K 31/74

(52) U.S. Cl. .............................. 424/401; 424/78.03

(58) Field of Search .................. 424/78.03, 401, 424/62, 64

(56) References Cited

U.S. PATENT DOCUMENTS

| | | | |
|---|---|---|---|
| 4,082,846 | 4/1978 | Clark | 424/266 |
| 4,699,924 | 10/1987 | Durrant et al. | 514/558 |
| 4,758,599 | 7/1988 | Minetti | 514/844 |
| 4,777,034 | 10/1988 | Olivier et al. | 424/65 |
| 4,873,085 | 10/1989 | Fuisz | 424/400 |
| 4,940,666 | 7/1990 | Boyce et al. | 435/240.2 |
| 4,944,937 | 7/1990 | McCall | 424/65 |
| 5,085,856 | 2/1992 | Dunphy et al. | 424/64 |
| 5,254,331 | 10/1993 | Mausner . | |
| 5,310,547 | 5/1994 | Dunphy et al. | 424/64 |
| 5,425,939 | 6/1995 | Guerrero et al. | 424/78.02 |
| 5,429,816 | 7/1995 | Hofrichter et al. | 424/66 |
| 5,449,512 | 9/1995 | Simmons | 424/73 |
| 5,472,687 | 12/1995 | Proctor | 424/70.1 |
| 5,496,827 | 3/1996 | Patrick | 514/310 |
| 5,527,350 | 6/1996 | Grove et al. | 607/89 |
| 5,571,794 | 11/1996 | Frome | 514/23 |
| 5,582,817 | 12/1996 | Otsu et al. | 424/59 |
| 5,593,662 | 1/1997 | Deckner et al. | 424/64 |
| 5,658,576 | 8/1997 | Soudant | 424/401 |
| 5,665,339 | 9/1997 | Simmons | 424/73 |
| 5,688,831 | 11/1997 | El-Nokaly et al. | 514/938 |
| 5,804,594 | 9/1998 | Murad | 514/474 |
| 5,833,998 | * 11/1998 | Biedermann et al. | 424/401 |
| 5,843,407 | * 12/1998 | El-Nokaly et al. | 424/64 |
| 6,024,976 | * 11/1998 | Miranda et al. | 424/449 |

FOREIGN PATENT DOCUMENTS

| | | | |
|---|---|---|---|
| 4328871 A1 | 3/1995 | (DE) | A61K/7/44 |
| 0 524 892 B1 | 7/1992 | (EP) | A61K/7/48 |
| 0 512814 A1 | 11/1992 | (EP) | A61K/7/48 |
| 0 522618 A1 | 1/1993 | (EP) | A61K/7/027 |
| 0 522624 A1 | 1/1993 | (EP) | A61K/7/027 |
| 0748622 A1 | 12/1996 | (EP) | A61K/7/025 |
| 0 852946 A2 | 7/1998 | (EP) | A61K/7/48 |
| 3203 | 3/1965 | (FR) . | |
| 2513879 | 4/1983 | (FR) | A61K/7/32 |
| 2694692 | 2/1994 | (FR) | A61K/7/48 |
| 61-063615 | 4/1986 | (JP) | A61K/9/06 |
| 61-83110 | 4/1986 | (JP) . | |
| 4-305512 | 10/1992 | (JP) | A61K/7/00 |
| 6-087730 | 3/1994 | (JP) | A61K/7/48 |
| 6-107531 | 4/1994 | (JP) | A61K/7/48 |
| 9-002952 | 1/1997 | (JP) | A61K/31/455 |
| 10-139676 | 5/1998 | (JP) | A61K/35/78 |
| 10-194954 | 7/1998 | (JP) | A61K/7/48 |
| 10-194958 | 7/1998 | (JP) | A61K/7/48 |
| 11-269054 | 10/1999 | (JP) | A61K/7/48 |
| WO 94/06400 | 3/1994 | (WO) | A61K/7/00 |
| WO 96/07396 | 3/1996 | (WO) | A61K/7/48 |
| WO 97/01345 | 1/1997 | (WO) | A61K/35/78 |
| WO 97/01346 | 1/1997 | (WO) | A61K/35/78 |
| WO 97/31620 | 9/1997 | (WO) | A61K/7/48 |
| WO 98/33475A1 | 8/1998 | (WO) | A61K/7/48 |
| 98/52530 | 11/1998 | (WO) | A61K/7/48 |
| WO 98/52927 | 11/1998 | (WO) | C07D/241/36 |

OTHER PUBLICATIONS

U.S. application No. 09/214,204, Brooks et al., filed Dec. 30, 1998.
U.S. application No. 09/214,193, Brooks et al., filed Dec. 30, 1998.
U.S. application No. 09/214,205, Brooks et al., filed Dec. 30, 1998.
U.S. application No. 09/214,194, Brooks et al., filed Dec. 30, 1998.
U.S. application No. 09/214,196, Brooks et al., filed Dec. 30, 1998.
"Niacinamide 99% Degussa Feed Grade", Jan. 27, 1998.
Saturday Morning Subspecialty Session: Stimulation of Collagen Type III mRNA Synthesis in Human Skin Fibroblasts by Nicotinamide. BK Tay, MZ Hussain, TK Hunt (intr. By LH Smith). Dept. of Stomatology and Dept. of Surgery, University of California, San Francisco. Feb. 9, 1991.

* cited by examiner

Primary Examiner—Thurman K. Page
Assistant Examiner—S. Howard
(74) Attorney, Agent, or Firm—Armina E. Matthews; Fumiko Tsuneki

(57) ABSTRACT

The present invention relates to cosmetic compositions, comprising:

a.) from about 0.01% to about 50%, by weight, of vitamin $B_3$ compound;

b.) from about 0% to about 90%, by weight, of an emollient component comprising from 0% to about 100%, by weight, of an oil liquid at ambient temperature;

c.) from about 0.01% to about 40%, by weight, of a polar solvent;

d.) from about 0% to about 90%, by weight, of a solidifying agent; and e.) from about 0% to about 90%, on an anhydrous basis, of a color wherein the vitamin $B_3$ compound is added to the composition such that the concentration of the vitamin $B_3$ compound exceeds the saturation solubility of the vitamin $B_3$ compound in the polar solvent.

20 Claims, No Drawings

COSMETIC COMPOSITIONS

FIELD OF THE INVENTION

The present invention relates to cosmetics containing partially dissolved crystalline vitamin $B_3$ compounds.

BACKGROUND OF THE INVENTION

Niacin, also known as vitamin $B_3$, is the common name for nicotinic acid. The physiologically active form of niacin is niacinamide, also a member of the vitamin $B_3$ family of compounds. Niacin and niacinamide (nicotinic acid amide) function in the body as components of two coenzymes: nicotinamide adenine dinucleotide (NAD) and nicotinamide adenine dinucleotide phosphate (NADP). Until recently, these vitamin $B_3$ compounds were used exclusively to treat niacin deficiency and pellegra.

Today, however, vitamin $B_3$ compounds have also found use in the area of skin care actives. British Patent 1,370,236 describes compositions for skin lightening containing 0.5% to 10% niacin. Similarly, U.S. Pat. No. 4,096,240 discloses the use of 0.1% to 10% niacinamide for skin lightening. Vitamin $B_3$ compounds have also been found useful in regulating the texture of human skin. See PCT application WO 97/39733, to Oblong et al.

However, when topically applied to the skin, only about 2–4% of the applied vitamin $B_3$ compound actually penetrates into the skin. Thus, there exists a need for cosmetic compositions comprising vitamin $B_3$ compounds which provide improved skin penetration of vitamin $B_3$ compounds. The present inventors have discovered that cosmetic compositions which incorporate vitamin $B_3$ compounds in a polar solvent such that the vitamin $B_3$ compound exceeds the saturation solubility of the polar solvent improves the overall skin penetration of the vitamin $B_3$ compound.

It is, therefore, an aspect of the present invention to provide cosmetic compositions comprising a polar solvent and vitamin $B_3$ compounds as undissolved crystals.

A further aspect of the present invention is to provide lipstick compositions comprising a polar solvent and vitamin $B_3$ compounds as undissolved crystals.

These and other aspects will become readily apparent from the detailed description which follows.

SUMMARY OF THE INVENTION

The present invention relates to cosmetic compositions, comprising:
- a.) from about 0.01% to about 50%, by weight, of vitamin $B_3$ compound;
- b.) from about 0% to about 90%, by weight, of an emollient component comprising from 0% to about 100%, by weight, of an oil liquid at ambient temperature;
- c.) from about 0.01% to about 80%, by weight, of a polar solvent;
- d.) from about 0%, to about 90%, by weight, of a surfactant;
- e.) from about 0% to about 90%, by weight, of a solidifying agent; and
- f.) from about 0% to about 90%, by weight, of a color wherein the vitamin $B_3$ compound is added to the composition such that the concentration of the vitamin $B_3$ compound exceeds the saturation solubility of the vitamin $B_3$ compound in the composition.

All percentages, parts and ratios are based upon the total weight of the cosmetic compositions of the present invention, unless otherwise specified. All such weights as they pertain to listed ingredients are based on the active level and, therefore, do not include carriers or by-products that may be included in commercially available materials, unless otherwise specified.

DETAILED DESCRIPTION OF THE INVENTION

As used herein the term "comprising" means that the composition can contain other ingredients which are compatible with the composition and which preferably do not substantially disrupt the compositions of the present invention. The term encompasses the terms "consisting of" and "consisting essentially of".

As used herein, the term "cosmetics" includes make-up, foundation, and skin care products. The term "make-up" refers to products that leave color on the face, including foundations, blacks and browns, i.e., mascara, concealers, eye liners, brow colors, eye shadows, blushers, lip colors, and so forth. Skin care products are those used to treat or care for, or somehow moisturize, improve, or clean the skin. Products contemplated by the phrase "skin care products" include, but are not limited to, adhesives, bandages, toothpaste, anhydrous occlusive moisturizers, antiperspirants, deodorants, powder laundry detergent, fabric softener towels, occlusive drug delivery patches, nail polish, powders, tissues, wipes, solid emulsion compact, hair conditioners-anhydrous and the like. The term "foundation" refers to liquid, creme, mousse, pancake, compact, concealer or like product created or reintroduced by cosmetic companies to even out the overall coloring of the skin. Foundation is manufactured to work better over moisturized and/or oiled skin.

ESSENTIAL COMPONENTS

Vitamin $B_3$ Component

The compositions of the present invention comprise a safe and effective amount of a natural or synthetic vitamin $B_3$ compound. The compositions of the present invention preferably comprise from above 0.01% to about 50%, more preferably from about 0.1% to about 30%, even more preferably 0.5% to about 20%, more preferably from about 1% to about 10% of the vitamin $B_3$ compound.

As used herein, "vitamin $B_3$ compound" means a compound having the formula:

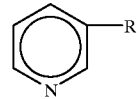

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Suitable esters of nicotinic acid include nicotinic acid esters of $C_1$–$C_{22}$, preferably $C_1$–$C_{16}$, more preferably $c_1$–$C_6$ alcohols. The alcohols are suitably straight-chain or branched chain, cyclic or acyclic, saturated or unsaturated (including aromatic), and substituted or unsubstituted. The esters are preferably non-rubifacient. As used herein, "non-rubifacient" means that the ester does not commonly yield a visible flushing response after application to the skin in the subject compositions (the majority of the general population would not experience a visible flushing response, although such compounds may cause vasodilation not visible to the naked eye). Alternatively, a nicotinic acid material which is rubifacient at higher doses could be used at a lower dose to reduce the rubifacient effect. Non-rubifacient esters of nicotinic acid include tocopherol nicotinate and inositol hexanicotinate; tocopherol nicotinate is preferred.

Other derivatives of the vitamin $B_3$ compound are derivatives of niacinamide resulting from substitution of one or more of the amide group hydrogens. Nonlimiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1–C18). Specific examples of such derivatives include nicotinuric acid and nicotinyl hydroxamic acid, which have the following chemical structures:

nicotinuric acid:

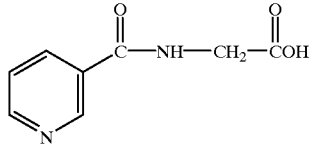

nicotinyl hydroxamic acid:

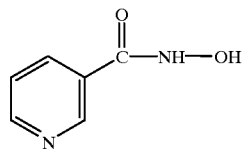

Exemplary nicotinyl alcohol esters include nicotinyl alcohol esters of the carboxylic acids salicylic acid, acetic acid, glycolic acid, palmitic acid and the like. Other non-limiting examples of vitamin $B_3$ compounds useful herein are 2-chloronicotinamide, 6-aminonicotinamide, 6-methylnicotinamide, n-methyl-nicotinamide, n,n-diethylnicotinamide, n(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, and niaprazine.

Examples of the above vitamin $B_3$ compounds are well known in the art and are commercially available from a number of sources, e.g., the Sigma Chemical Company (St. Louis, Mo.); ICN Biomedicals, Inc. (Irvin, Calif.) and Aldrich Chemical Company (Milwaukee, Wis.).

One or more vitamin $B_3$ compounds may be used herein. Preferred vitamin $B_3$ compounds are niacinamide and tocopherol nicotinate. Niacinamide is more preferred.

When used, salts, derivatives, and salt derivatives of niacinamide are preferably those having substantially the same efficacy as niacinamide in the methods of regulating skin condition described herein.

Salts of the vitamin $B_3$ compound are also useful herein. Nonlimiting examples of salts of the vitamin $B_3$ compound useful herein include organic or inorganic salts, such as inorganic salts with anionic inorganic species (e.g., chloride, bromide, iodide, carbonate, preferably chloride), and organic carboxylic acid salts (including mono-, di- and tri-C1–C18 carboxylic acid salts, e.g., acetate, salicylate, glycolate, lactate, malate, citrate, preferably monocarboxylic acid salts such as acetate). These and other salts of the vitamin $B_3$ compound can be readily prepared by the skilled artisan, for example, as described by W. Wenner, "The Reaction of L-Ascorbic and D-Isoascorbic Acid with Nicotinic Acid and Its Amide", J. Organic Chemistry, VOL. 14, 22–26 (1949), which is incorporated herein by reference. Wenner describes the synthesis of the ascorbic acid salt of niacinamide.

In a preferred embodiment, the ring nitrogen of the vitamin $B_3$ compound is substantially chemically free (e.g., unbound and/or unhindered), or after delivery to the skin becomes substantially chemically free ("chemically free" is hereinafter alternatively referred to as "uncomplexed"). More preferably, the vitamin $B_3$ compound is essentially uncomplexed. Therefore, if the composition contains the vitamin $B_3$ compound in a salt or otherwise complexed form, such complex is preferably substantially reversible, more preferably essentially reversible, upon delivery of the composition to the skin. For example, such complex should be substantially reversible at a pH of from about 5.0 to about 6.0. Such reversibility can be readily determined by one having ordinary skill in the art.

More preferably the vitamin $B_3$ compound is substantially uncomplexed in the composition prior to delivery to the skin. Exemplary approaches to minimizing or preventing the formation of undesirable complexes include omission of materials which form substantially irreversible or other complexes with the vitamin $B_3$ compound pH adjustment, ionic strength adjustment, the use of surfactants, and formulating wherein the vitamin $B_3$ compound and materials which complex therewith are in different phases. Such approaches are well within the level of ordinary skill in the art.

Thus, in a preferred embodiment, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably, essentially free of the salt form. The vitamin $B_3$ compound in the compositions hereof having a pH of from about 4 to about 7 typically contain less than about 50% of the salt form.

The vitamin $B_3$ compound may be included as the substantially pure material, or as an extract obtained by suitable physical and/or chemical isolation from natural (e.g., plant) sources. The vitamin $B_3$ compound is preferably substantially pure, more preferably essentially pure.

The cosmetic compositions of the present invention comprise the vitamin $B_3$ compound and the polar solvent at concentrations such that the concentration of the vitamin $B_3$ compound exceeds the saturation solubility (at ambient temperature, say, at about 20° C.) of the vitamin $B_3$ compound in the composition. As a result, a portion of the vitamin $B_3$ compound is present in undissolved form. Preferably, the concentration of the vitamin $B_3$ compound will be at least 50% greater than the saturation solubility at ambient temperature, more preferably at least 100% greater than the saturation solubility at ambient temperature and most preferably at least 150% greater or more than the saturation solubility at ambient temperature of the vitamin $B_3$ compound in the composition.

Polar Solvent

Solvents suitable for use in the present invention include any polar solvent capable of dissolving the vitamin $B_3$ compound. Suitable polar solvents include: water, alcohols, such as ethanol, propyl alcohol, isopropyl alcohol, hexanol, and benzyl alcohol; polyols, such as propylene glycol, polypropylene glycol, butylene glycol, hexylene glycol, maltitol, sorbitol, and glycerine; panthenol dissolved in glycerine, flavor oils, and mixtures thereof. Mixtures of these solvents can also be used. Preferred polar solvents are polyhydric alcohols and water. Examples of preferred solvents include glycerine, panthenol in glycerine, glycols such as propylene glycol and butylene glycol, polyethylene glycols, water and mixtures thereof. The most preferred polar solvents for use are alcohols, glycerine, panthenol, propylene glycol, butylene glycol hexylene glycol and mixtures thereof.

Typically, the cosmetic compositions of the present invention will comprise from about 0.1% to about 80%, preferably from about 0.5% to about 60%, more preferably from about 1% to about 30% and most preferably from about 3% to about 18% polar solvent.

Optional Components

Emollient Component

Also essential to the compositions of the present invention is an emollient component. The emollient component can comprise fats, oils, fatty alcohols, fatty acids and esters which aid application and adhesion, yield gloss and most importantly provide occlusive moisturization.

Suitable emollients for use are isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients can be found in the Cosmetic Bench Reference, pp. 1.19–1.22 (1996).

Particularly preferred emollients are polar emollient emulsifiers such as linear or branched chained polyglycerol esters. By "polar emollient," as used herein, means any emollient emulsifier having at least one polar moiety and wherein the solubility (at 30° C.) of the vitamin $B_3$ compound is in the polar emollient is greater than about 1.5%, preferably greater than about 2%, more preferably greater than about 3%. Suitable polar emollients include, but are not limited to, polyol ester and polyol ethers such as linear or branched chained polyglycerol esters and polyglycerol ethers. Nonlimiting examples of such emollients include PG3 diisostearate, polyglyceryl-2-sesquiisostearate, polyglyceryl-5-distearate, polyglyceryl-10--distearate, polyglyceryl-10-diisostearate, acetylated monoglycerides, glycerol esters, glycerol tricaprylate/caprate, glyceryl ricinoleate, glyceryl isostearate, glyceryl myristate, glyceryl linoleate, polyalkylene glycols such as PEG 600, monoglycerides, 2-monolaurin, sorbitan esters and mixtures thereof.

Also preferred are non-polar emollients. By "non-polar emollient," as used herein, means any emollient emulsifier possessing no permanent electric moments and wherein the solubility (at 30° C.) of the vitamin $B_3$ compound is in the polar emollient is less than about 1.5% preferably less than about 1.0%, more preferably less than about 0.5%. Suitable non-polar emollients include, but are not limited to, esters and linear or branched chained hydrocarbons. Nonlimiting examples of such emollients isononyl isononanoate, isopropyl isostearate, octyl hydroxystearate, diisopropyl dimerate, lanolin oil, octyl palmitate, isopropyl palmitate, pariffins, isoparrifins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof.

The solubility of the vitamin $B_3$ compound in polar or non-polar emollients is determined as set forth below.

Suitable oils include esters, triglycerides, hydrocarbons and silicones. These can be a single material or a mixture of one or more materials. They will normally comprise from 0% to about 100%, preferably from about 5% to about 90%, and most preferably from about 70% to about 90% of the emollient component.

Oils act as emollients and also impart viscosity, tackiness, and drag properties to cosmetic compositions such as lipstick. Examples of suitable oils include caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hyroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, sheabutter, octylpalmitate, maleated soybean oil, glycerol trioctanoate, diisopropyl dimerate, and volatile and non-volatile silicone oils including phenyl trimethicone.

The preferred oils for use herein are acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglyerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

Preferably, the oils used are selected such that the majority (at least about 75%, preferably at least about 80% and most preferably at least about 99%) of the types of oils used have solubility parameters which do not differ by more than from about 1 to about 0.1, preferably from about 0.8 to about 0.1.

The emollient component comprises from about 1% to about 90%, preferably from about 10% to about 80%, more preferably from about 20% to about 70%, and most preferably from about 40% to about 60%, of the cosmetic composition.

Surfactants

Surfactants suitable for use are those which can form emulsions and/or association structures. Surfactant emulsifier can be from 0% to about 20% of the formulation, preferably from 0% to about 15% and most preferably from about 1% to about 10%. Examples of suitable emulsifiers can be found in U.S. Pat. No. 5,085,856 to Dunphy et al.; Japanese Patent Publication Sho 61-83110; European Patent Application EP 522624 to Dunphy et al.; U.S. Pat. No. 5,688,831 to El-Nokaly et al. Examples of other suitable emulsifiers can be found in Cosmetic Bench Reference, pp. 1.22, 1.24–1.26 (1996), all of which are herein incorporated by reference in its entirety.

Also useful herein are surfactants which form association structures, preferably lamellar or hexagonal liquid crystals, at ambient temperature when mixed with a polar solvent. Ambient temperature/room temperature as used herein typically means about 20° C. Generally ambient temperature can range from about 18° C. to about 27° C., preferably from about 20° C. to about 25° C., depending on such variables as geographical location, i.e. sub-tropical vs. temperature regions. One of ordinary skill in art is able to determine if association structures form at ambient temperatures. The surfactants suitable for use generally have a Krafft point at or below about ambient temperature about 20° C. or generally at or below about 18° C. to about 27° C., preferably at or below from about 20° C. to about 25° C.

The definition of Krafft point is well known in the art and one of ordinary skill in the art can determine a surfactant's Krafft point. In general terms, Krafft point is the melting point of the hydrocarbon chains of the surfactants. It can also be expressed as the temperature at which the solubility of an association colloid in water suddenly increases because critical micelle concentration is exceeded and micelles form. See Ekwall., P., "Composition, Properties and Structure of Liquid Crystalline 1Phases in Systems of Amphiphilic Compounds " *Advances in Liquid Crystals* Vol. 1, Chapter 1, p.81.

In preparing a sample combination of surfactant and polar solvent to demonstrate the ability to form association structures, the surfactant needs to be sufficiently soluble in the polar solvent such that an association structure can form at ambient temperature. One of ordinary skill in the art is capable of determining compatible interactions.

Any surfactant which forms association structures at ambient temperature and is suitable for use in cosmetics is suitable for use herein. Surfactants suitable for use in cosmetics do not present dermatological or toxicological problems. Anionic surfactants, nonionic surfactants, cationic surfactants, amphoteric surfactants and mixtures thereof are suitable for use. Preferably anionic surfactants, nonionic surfactants, cationic surfactants, amphoteric surfactants and mixtures thereof having a Krafft point at or below about ambient temperature are used. More preferably, nonionic surfactants, cationic surfactants, amphoteric surfactants and mixtures thereof having a Krafft point at or below about ambient temperature are used.

Surfactants suitable for use in forming association structures are found in U.S. Pat. No. 5,843,407 to El-Nokaly, herein incorporated by reference.

The association structures of the present invention are also useful in improving the skin penetration of the vitamin $B_3$ compound. Without being limited by theory, the association structures are believed to act as occlusives on the skin by forming continuous or discontinuous bi-layer or multi-layer films on the skin. The term "occlusive," as used herein, means a preventing or obstructing something, in this case, preventing the removal of moisture (via evaporation) and the vitamin $B_3$ compound (via film binding) from the surface of the skin. Furthermore, since the association structures of the present invention are thermodynamically stable, it is believed that the entrapped or bound polar solvent is slowly released over time. The slow release of the polar solvent thereby aids in maintaining the vitamin $B_3$ compound in solubilized form, thus, improving skin penetration of the vitamin $B_3$ compound. This occlusive effect is even further enhanced by the addition of the waxy or wax-like (or gel-like) solidifying agents disclosed above.

The surfactants can be used at levels from about 4% to about 97%, preferably from about 5% to about 95%, more preferably from about 20% to about 90% and most preferably from about 30% to about 70% of the association structure.

Solidifying Agent

The cosmetic compositions of this invention can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 3% to about 20%.

The wax cosmetic stick embodiments of this invention preferably contain from about 5% to about 50% (by weight) of a waxy solidifying agent. By the term "waxy solidifying agent," as used herein, is meant a solidifying material having wax-like characteristics. Such waxy materials may also serve as emollients. Among the waxy materials useful herein are the high melting point waxes, i.e., having a melting point of from about 65° C. to about 125° C., such as beeswax, spermaceti, carnauba, baysberry, candelilla, montan, ozokerite, ceresin, paraffin, synthetic waxes such as Fisher-Tropsch waxes, microcrystalline wax, and mixtures thereof. Ceresin, ozokerite, white beeswax, synthetic waxes, and mixtures thereof, are among those useful herein are disclosed in U.S. Pat. No. 4,049,792, Elsnau, issued Sep. 20, 1977, herein incorporated by reference in its entirety). Low melting waxes, having a melting point of from about 37° C. to about 75° C., are preferred for use in the wax stick embodiments of this invention. Wax stick embodiments of this invention, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acid amides, having fatty chains of from about 8 to about 30 carbon atoms, and mixtures thereof. Preferred wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are particularly preferred. Fatty acids, fatty alcohols, and other wax-like materials useful in this invention are also disclosed in the following refences, all of which are incorporated by reference herein: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; "The Chemistry and Technology of Waxes". A. H. Warth, 2nd Edition, reprinted in 1960, Reinhold Publishing Corporation, pp. 391–393 and 421; "The Petroleum Chemicals Industry", R. F. Goldstein and A. L. Waddeam, 3rd Edition (1967), E & F. N. Span Ltd., pp 33–40; "The Chemistry and Manufacture of Cosmetics", M. G. DeNavarre, 2nd edition (1970), Van Nostrand & Company, pp 354–376; and in "Encyclopedia of Chemical Technology:, Vol. 24, Kirk-Othmer, 3rd Edition (1979) pp 466–481. Preferred wax-like materials useful as solidifying agents in the present wax sticks are described in U.S. Pat. No. 4,126,679, Davy, et al., issued Nov. 21, 1978, herein incorporated by reference in its entirety. Preferred mixtures of wax-like materials comprise fatty alcohols containing carbon chains of from about 14 to about 18 carbon atoms, and alcohols having chain lengths of 20 carbons or longer, wherein the final mixture contains from about 1% to about 3% (by weight) of the longer-chain fatty alcohols. Compositions containing these fatty alcohol mixtures and described in European Patent Specification No. 117,070, May, published Aug. 29, 1984 (incorporated by reference herein).

Also useful herein are biopolymers such as those described in European Application No. 522624, to Dunphy et al., herein incorporated by reference in its entirety.

The gel stick embodiments of this invention preferably contain from about 3% to about 30%, preferably from about 3% to about 10% (by weight), of a solidifying agent. The particular amount of solidifying agent to be used will depend upon the particular solidifying agent and the liquid base material used, and the desired physical characteristics of the gel stick. Solidifying agents useful in the gel stick embodiments of this invention are, in general, surface-active compounds which form networks immobilizing or solidifying the liquid base materials into a gel. Such solidifying agents include: soaps, such as the sodium and potassium salts of higher fatty acids, i.e., acids having from 12 to 22 carbon atoms; amides of higher fatty acids; higher acid fatty acid amides of alkylolamines; dibenzaldehyde-monosorbitol acetals; alkali metal and alkaline earth metal salts of the acetates, propionates and lactates; waxes, such as candelilla and carnauba waxes; and mixtures thereof. Among those solidifying agents preferred for use in the gel stick embodiments of this invention are sodium stearate, sodium palmitate, aluminum stearate, aluminum magnesium hydroxy stearate, and mixtures thereof. Gel stick compositions containing solidifying agents among those useful herein are described in the following patent documents, all incorporated herein by reference in their entirety: U.S. Pat. No. 2,900,306, Slater issued Aug. 18, 1959; U.S. Pat. No. 3,255,082, Barton, issued Jun. 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; and U.S. patent application Ser. No. 630,790, DiPietro, filed Jul. 13, 1984. Preferred solidifying agents useful in the gel stick embodiments of the present invention are described in European Patent Specification No. 24,365 Sampson, et al., published Mar. 4, 1981, incorporated herein by reference in its entirety.

Also useful herein as solidifying agents are conventional thickening agents. Examples of suitable thickeners include, but are not limited to, naturally-occurring polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate. Naturally occuring polymers or biopolymers and their use are further described in European Application No. 522624, to Dunphy et al. Additional examples of naturally occurring polymers or biopolymers can be found in the Cosmetic Bench Reference, pp. 1.40–1.42, herein incorporated by reference.

Also useful herein are hydrophilic gelling agents such as the acrylic acid/ethyl acrylate copolymers and the carboxyvinyl polymers sold by the B. F. Goodrich Company under the trademark of Carbopol Registered TM resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentacrythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10–30 Alkyl Acrylate Crosspolymer). Combination of the above polymers are also useful herein. Other gelling agents suitable for use herein include oleogels such as trihydroxystearin.

Hydrophobically modified celluloses are also suitable for use herein. These celluloses are described in detail in U.S. Pat. Nos. 4,228,277 and 5,104,646, both of which are herein incorporated by reference in their entirety.

Additional examples of suitable gelling agents or gellants can be found in the Cosmetic Bench Reference, p. 1.27, herein incorporated by reference.

Without being limited by theory, the solidifying agent in combination with the emollient is believed to act as an occlusive on the skin by forming continuous or discontinuous bi-layer or multi-layer films on the skin. The term "occlusive," as used herein, means a preventing or obstructing something, in this case, preventing the removal of moisture (via evaporation) and the vitamin $B_3$ compound (via film binding) from the surface of the skin.

Color

Certain embodiments of the present invention, preferably lipsticks or lip paints, contain from 0% to about 90%, preferably from about 1% to about 35%, more preferably from about 1% to about 20% and most preferably from about 5% to about 15%, of color, on an anhydrous pigment weight basis. These are usually aluminum, barium or calcium salts or lakes. Preferably, dyes are present at from about 0.1% to about 4% and pearls from 0% to about 20%.

Pigments are typically dispersed in emollients for the good dispersion of the pigments when incorporated into the lip compositions, thus providing an even distribution of color. Excellent dispersion of the pigment can be achieved by utilizing association structures, preferably lamellar liquid crystals, as a means of incorporating the color/pigments into the cosmetic compositions of the present invention. A preferred method of incorporating dry pigments comprises the steps of:

(a) preparing a mixture consisting essentially of:
 (1) a polar solvent; and
 (2) a surfactant selected from the group consisting of amphoteric, cationic, anionic and nonionic surfactants having a Krafft point at or below about ambient temperature and mixtures thereof; and (b) stirring said mixture until association structures form;

(c) adding and mixing dry pigments until achieving a homogeneous mixture;

(d) milling said mixture until uniform particle size is achieved; and (e) adding and mixing the mixture of (c) to the remaining ingredients until a homogeneous mixture is obtained.

If the ingredients of the cosmetic composition are being processed such that the association structures are being formed in situ, the preferred method of incorporating the dry pigments is to slurry them in one or more of the liquid emollient ingredients.

Colors/pigments suitable for use herein are all inorganic and organic colors/pigments suitable for use in lipstick compositions.

Lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein. Lakes suitable for use in the present invention include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors and pigments can also be included in the lipsticks, such as dyes and pearls, titanium oxides, Red 6, Red 21, Brown, Russet and Sienna dyes, chalk, talc, iron oxides and titanated micas.

Perferably, the color component is water-insoluble particulate solids having an average particle size diameter of less than about 5 microns, more preferably 2 microns, most preferably 1 micron.

Without being limited by theory, it is believed that such solid particulates position themselves at the interface of dispersed droplets (i.e., the discontinuous phase) and the continuous phase to serve as barriers, preventing the coalescence of the dispersed droplets and, hence, improving stabilization. A more detailed explanation of this phenomenon is described in S. E. Friberg and Kåre Larsson, Food Emulsions, pp. 36–41, Marcel Dekker, Inc. (1997), herein incorporated by reference it its entirety.

Dispersants may also be used in conjunction with the colors and pigments of the present invention. Examples of suitable dispersants include, but are not limited to, those described in U.S. Pat. No. 5,688,493, herein incorporated by reference in its entirety.

Dermatologically Acceptable Cosmetic Carrier

The composition of the present invention in association with a cosmetically or dermatologically acceptable cosmetic vehicle or carrier. Such a carrier is compatible with the skin, the nails, the mucous membranes, tissues and the hair and includes any conventionally used cosmetic or dermatological carrier which meets these requirements. Such a carrier is also compatible with the vitamin $B_3$ compound, that is the carrier should not interact with the vitamin $B_3$ compound. Suitable carriers include, but are not limited to, solutions, soaps, bodywashes, emulsions, ointments, lipsticks, foundations, mascaras, powders, suspensions, creams, lotions, gels, foams, mousses and the like. These carriers facilitate topical application and, in some cases, provide additional therapeutic effects, e.g., by moisturizing of the affected skin areas. Dermatologically acceptable cosmetic carriers can be readily selected by one of ordinary skill in the art.

Other Additives

Other optional ingredients which can be present in the cosmetic compositions of the present invention include the flavor oils which were described above, fat soluble vitamins such as vitamin A and E, esters of vitamin A (e.g., acetate, propionate, or palmitate) and of vitamin E (e.g., acetate or sorbate), sunscreens such as octyl methoxycinnamate and butyl methoxydibenzoylmethane, sunblocks such as titanium dioxide and zinc oxide, germicides such as triclosan, anti-inflammatory agents such as hydrocortisone, lipid materials such as ceramides and liposomes and skin care actives. The cosmetic compositions can comprise ingredients conventionally employed in cosmetic compositions such as mascara, foundation or lipcare products. This includes skin care active ingredients such as pharmaceutically active ingredients.

Skin care actives ingredients in both water soluble and water insoluble forms can be added to the cosmetic compositions of the present invention. These include, but are not limited to vitamin C and its derivatives (e.g., ascorbyl palmitate, ascorbyl phosphate and its salts such as magnesium or sodium), vitamin D, panthenol, retinoic acid, zinc oxide, beta-glycyerhetic acid; chamomile oil; ginko biloba extract; pyroglutamic acid, salts or esters; sodium hyaluronate; 2-hydroxyoctanoic acid; sulfur; salicylic acid; carboxymethyl cysteine, and mixtures thereof.

These additives, both fat soluble and water soluble, will normally be present in amounts of less than about 10% by weight, and generally in the range of about 0.01% to about 5%, preferably from about 0.01% to about 3%, most preferably from about 0.1% to about 1%, by weight.

Flavor oils such as peppermint oil, orange oil, citrus oil, wintergreen oil can be used along with an alcohol or glycerine. Flavor oils are usually mixed in a solvent such as ethanol to dilute the flavor. The flavor oils useful herein can be derived from natural sources or be synthetically prepared. Generally flavor oils are mixtures of ketones, alcohols, fatty acids, esters and terpenes. The term "flavor oil" is generally recognized in the art to be a liquid which is derived from botanical sources, i.e. leaves, bark, or skin or fruits or vegetables, and which are usually insoluble in water. The level of flavor oil used can range from 0% to about 5%, preferable from 0% to about 1%.

Moisturizers may also be included into the present compositions. Preferred moisturizers include pyrrolidone carboxylic acid, sodium lactate or lactic acid, urea, guanidine, glyceric acid and its salts (e.g., calcium salt), petrolatum, collagen, α-hydroxy propylglyceryl ether, α-hydroxy acids (e.g., ethylglycolic acid, leucic acid, mandelic acid, glycolic acid), glucosamines, and elastin fibers, D-panthenol, allantoin and hyaluronic acid and chondroitin sulfate. Examples of suitable moisturizers can be found in Cosmetic Bench Reference, p. 1.30–1.32 (1996), herein incorporated by reference.

A preferred optional component is ethyl cellulose (Ethocel). Ethyl cellulose generally is preferred for use at levels of about 5% and more preferably 1%.

Another preferred optional component is silica. Silica is generally preferred for use at levels of from about 1% and about 5%.

Hypoallergenic compositions can be made from the liquid crystal, wax, oil and colors herein. These compositions should not contain fragrances, flavor oils, lanolin, sunscreens, particularly PABA, or other sensitizers or potential sensitizers and irritants.

The compositions of the present invention can also be made into long lasting or non-transferable cosmetic compositions. Detailed discussions of such lipsticks are found in Japanese Patent Publication Hei No. 6-199630 and European Patent Application 748622, both of which are herein incorporated by reference in their entirety.

Additional optional materials that can be incorporated in the compositions of the present invention can be found in PCT application WO 97/39733, to Oblong et al.

METHODS OF USE

The cosmetic compositions of the present invention are ideally suited for use in treating the skin and lips, especially in the form of a lipstick or lip balm for applying to the lips a permanent or semi-permanent color, ideally with a gloss or luster finish. The cosmetic compositions can also be used in treating the skin and/or lips with a skin care agent for protection against exposure to adverse weather, including the wind and rain, dry and/or hot environments, environmental pollutants (e.g., ozone, smoke, and the like), or exposure to excessive doses of sunlight. The compositions are also useful in providing sun protection, moisturizing and/or conditioning for the hair and skin, improved skin feel, regulating skin texture, reducing fine lines and wrinkles, reducing oily shine on hair or skin, skin lightening and reducing skin or hair odor.

The cosmetic compositions can accordingly, be applied to the skin and/or lips in the traditional manner with or without a conventional holder or applicator to provide a decorative and/or protective film thereto.

Methods of Determining Solubility of Vitamin $B_3$ Compounds in Emollients

The solubility of the vitamin $B_3$ compound in the various polar and non-polar emollients of the present invention can be determined as follows:

I. Preparation of Samples for Analysis:
1) the emollient is placed in pre-weighted vial and the saturated with a vitamin $B_3$ compound;
2) the vial is shaken and allowed to sit in a bath at 30° C. for 1 hour. A small stir bar is used to agitate the contents of the vial. If no precipitation occurs in the vial, then more niacinamide is added. This was repeated until precipitation occurred. The sample is left in the bath for an additional 48 hours to insure saturation;
3) the saturated emollient is drawn into a syringe;
4) A 0.45 micron filter (Gelman Acrodisc) is fitted on the end the syringe and the emollient is filtered through into separate pre-weighted vial for analysis;
5) The emollient is analyzed using HPLC to determine the amount of niacinamide therein.

II. Analysis

Approximately 0.25 g of the sample is weighed (sample weight) into a 15 mL plastic screw-cap centrifuge tube. The sample is mixed with approximately 3 mL of 50/50 v/v methanol/chloroform and homogenized by vortex mixing. About 7 mL of water is then added to extract the vitamin $B_3$ compound from the methanol/chloroform phase. Each sample is mixed by shaking 50 times in a back and forth motion to facilitate transfer of the niacinamide from the methanol/chloroform to the water phase. This mixing creates an emulsion at the interface of the two phases. The emulsion can be dissipated by letting the sample stand for several hours or by brief centrifugation (15 seconds) at high speed. Once the two phases have completely separated, a pipette is used to carefully transfer the aqueous phase into a separate, pre-weighted vial. The weight of the aqueous phase is noted (aqueous phase weight). An aliquot of the aqueous phase is transferred to an analysis container and analyzed for niacinamide by HPLC (Waters 2690 Separations Module coupled with a Waters 996 PDA detector, both supplied by Waters Corporations).

III. Calculations

The percent vitamin $B_3$ compound is determined by taking the vitamin $B_3$ compound concentration measured by HPLC and multiplying by the dilution factor. The dilution factor is the aqueous phase weight divided by the sample weight.

EXAMPLES

The cosmetic formulations illustrated in Examples I–XI illustrate specific embodiments of the cosmetic compositions of the present invention, but are not intended to be limiting thereof. Other modifications can be undertaken by the skilled artisan without departing from the spirit and scope of this invention. These exemplified embodiments of the cosmetic compositions of the present invention provide improve the skin penetration of the vitamin $B_3$ compound as well as improve the improve the stability of the cosmetic composition.

All exemplified compositions can be prepared by conventional formulation and mixing techniques. Such formulation and mixing techniques are described in detail in *Harry's Cosmeticology*, pp. 119–141 and 314–354 (J. B. Wilkinson and R. J. Moore $7^{th}$ ed 1982), and *Cosmetics: Science and Technology*, pp. 1–104 and 307–422 (M. S. Balsam and E. Sagarin $2^{nd}$ ed 1972), both of which are herein incorporated by reference in its entirety. Component amounts are listed as weight percents and exclude minor materials such as diluents, fillers, and so forth. The listed formulations, therefore, comprise the listed components and any minor materials associated with such components.

Example I

A lipstick composition of the present invention is prepared as follows:

| Ingredient | Amount (weight percent) |
| --- | --- |
| Castor Oil | 13.5 |
| Isopropyl palmitate | 11.6 |
| Caprylic/capric/isostearic/adipic triglyceride | 7.0 |
| Lanolin | 7.0 |
| Red 21 Aluminum Lake | 7.0 |

-continued

| Ingredient | Amount (weight percent) |
|---|---|
| Candelilla wax | 6.6 |
| Propylene glycol myristyl ether acetate | 6.0 |
| Caprylic/capric triglyceride | 5.8 |
| Glycerol | 5.0 |
| Water | 5.0 |
| Niacinamide | 6.0 |
| Titanium dioxide | 4.7 |
| Beeswax | 4.1 |
| Monoglyceride | 3.5 |
| Lanolin oil | 2.5 |
| Ozokerite wax | 2.5 |
| Phospholipid (soybean lecithin) | 1.0 |
| Polybutene | 0.8 |
| Carnauba wax | 0.4 |

The above ingredients are added to a stainless steel vessel equipped with a heating source. The ingredients are heated to about 85° C. and mixed until a homogeneous. This mixture is then poured into a mold and cooled to room temperature.

The lipstick is applied to the lips to provide color, moisturization and improved lip feel.

Example II

A lipstick composition of the present invention is prepared as follows:

| Ingredient | Amount (weight percent) |
|---|---|
| Carnauba | 1.50 |
| Ozokerite | 6.00 |
| Candelillia | 4.00 |
| Hydrogenated Vegetable Oil | 5.00 |
| Acetylated Lanolin | 4.00 |
| Isopropyl Isostearate | 11.90 |
| Isostearic Acid | 10.00 |
| Propylparaben | 0.10 |
| Cetyl Ricinoleate | 10.00 |
| Ascorbyl Palmitate | 1.00 |
| Silica L-700 | 1.00 |
| Polybutene | 2.00 |
| Petrolatum | 5.50 |
| Association Structure Phase | |
| Sucrose Monooleate[1] | 12.00 |
| Niacinamide | 5.00 |
| Glycerine | 12.00 |
| Pigment | 9.00 |

[1]Ryoto Sugar Ester 0-1690, Mitsubishi-Kagaku Foods Corp.

The ingredients for the Association Structure Phase, except for the pigments, are mixed until association structures are formed. Once the association structures are formed, the pigments are added and the mixture is milled on a three roll mill. The mixture is then mixed, with the other ingredients and mixed until a homogeneous mixture. (Or, alternatively, the above components are added and mixed together at the same time.) This mixture is heated to 85° C. The mixture is then deaerated by vacuum and poured into the appropriate mold. The mixture is cooled to ambient temperature and incorporated into the appropriate package.

The lipstick is applied to the lips to provide color, moisturization and improved lip feel.

Example III

A lipstick composition of the present invention which is substantially free of castor oil, is prepared as follows:

| Ingredient | Amount (weight percent) |
|---|---|
| Carnauba | 1.50 |
| Ozokerite | 6.00 |
| Candelillia | 4.00 |
| Hydrogenated Vegetable Oil | 5.00 |
| Isopropyl Palmitate | 9.40 |
| Isostearic Acid | 7.50 |
| Acetylated Lanolin | 4.00 |
| Propylparaben | 0.10 |
| Cetyl Ricinoleate | 10.00 |
| Ascorbyl Palmitate | 1.00 |
| Silica L-700 | 1.00 |
| Polybutene | 2.00 |
| Petrolatum | 5.50 |
| Association Structure Phase | |
| Sucrose Monooleate[1] | 12.00 |
| Niacinamide | 10.00 |
| Glycerine | 12.00 |
| Pigment | 9.00 |

[1]Ryoto Sugar Ester 0-1690, Mitsubishi-Kagaku Foods Corp.

The composition is prepared as in Example II:

Example IV

A lipstick composition of the present invention which is substantially free of castor oil, is prepared as follows:

| Ingredient | Amount (weight percent) |
|---|---|
| Carnauba | 1.50 |
| Ozokerite | 5.50 |
| Candelillia | 4.00 |
| Hydrogenated Vegetable Oil | 8.50 |
| Acetylated Lanolin | 4.00 |
| Propylparaben | 0.10 |
| Cetyl Ricinoleate | 10.00 |
| Ascorbyl Palmitate | 1.00 |
| Polybutene | 2.00 |
| Polysiloxane Copolymer[1] | |
| Petrolatum | 5.97 |
| Anhydrous Lanolin | 5.97 |
| Association Structure Phase | |
| Lecithin | 22.95 |
| Nicotinic acid | 2.50 |
| Panthenol | 5.04 |
| Glycerine | 12.00 |
| Pigment | 9.00 |

[1] #1154-141-1, supplied by GE Silicones.

The composition is prepared as in Example II.

Example V

An antiperspirant gel stick of the present invention is prepared as follows:

| Ingredient | Amount (weight percent) |
|---|---|
| N-Lauroyl-L-glutamic acid-di-n-butyl amide[1] | 4 |
| 12-hydroxystearic acid | 2 |

-continued

| Ingredient | Amount (weight percent) |
| --- | --- |
| Propylene Glycol | 0.1 |
| Tocopherol nicotinate | 2 |
| Light mineral oil[2] | 23 |
| Diisopropyl Sebacate[3] | 43 |
| Aluminum Zirconium | 25 |
| Talc | 3 |

[1]GP-1 supplied by Ajinomoto, Inc.
[2]Benol White Mineral Oil supplied by Witco Chemical Corp.
[3]Schercemol DIS supplied by Scher Cherfficals Inc.

The gelling agent and the liquid base material are combined into a vessel equipped with a heat source. Heat the mixture to between about 80° C. and about 130° C. with stirring, until the mixture forms a homogeneous, molten solution. Preferably, the homogeneous, molten solution is allowed to cool to a mixing temperature, typically between about 65° C. and 120° C. (Alternatively, the mixture may simply be heated to the mixing temperature until the mixture forms a homogeneous, molten solution. This alternative method, however, typically takes longer than heating at high temperatures and then cooling.) Add the tocopherol nicotinate, propylene glycol, antiperspirant active and other ingredients, such as fragrances and colors, into the homogeneous, molten solution in the above vessel with stirring. Allow the mixture to cool until it begins thickening and then pour the mixture into containers allowing them to cool to ambient temperature. (Although not preferred, the antiperspirant active may alternatively be added along with the gelling agent and the liquid base material in the first step.).

An antiperspirant composition, comprised as above, is applied to the underarm area of a human subject, and reduces the perspiration in the applied area and improves odor in this area.

Example VI

A solid antiperspirant stick of the present invention is prepared as follows:

| Ingredient | Amount (weight percent) |
| --- | --- |
| Stearyl Alcohol | 10.0 |
| Niacinamide | 5 |
| Butylene Glycol | 0.2 |
| Hydrogenated Castor Oil-mp 86 degrees C. | 4.0 |
| Aluminum Chlorohydroxide | 40.0 |
| Isopar "V"[1] | 45.0 |
| Fragrance | 1.0 |
| | 100.0 |

[1](Isopar "V", Avg. Mol. Wt. 197 B.P. Range, 255–301 degrees C.)

Heat the isoparaffin liquids, the water-insoluble liquid emollients, the surface active agent and the water-insoluble waxes to a temperature sufficient to form a solution of these materials, followed by the addition of the active astringent antiperspirant salts and niacinamide with gentle agitation. Following addition of the salts, other optional ingredients such as talc may then be added and mixed until a homogenous suspension is formed. The suspension is cooled to a temperature above the solidification point and is then poured into suitable containers.

An antiperspirant composition, comprised as above, is applied to the underarm area of a human subject, and reduces the perspiration in the applied area and improves odor in this area.

Example VII

A solid antiperspirant stick of the present invention is prepared as follows:

| Ingredient | Amount (weight percent) |
| --- | --- |
| Stearic Acid | 10.0 |
| Hydrogenated Castor Oil-mp 86 degrees C. | 4.0 |
| Zirconium Chlorohydroxide | 25.0 |
| Talc | 10.0 |
| Isopar "M" | 45.0 |
| Propylene Glycol | 0.5 |
| Niacinamide | 2.0 |
| Diisopropyl Adipate | 5.0 |
| Fragrance | 1.0 |
| | 100.0 |

[1](Isopar "M", Avg. Mol. Wt. 191 B.P. Range, 207–260 degrees C.)-In one

The composition is prepared and used as Example VI.

Example VIII

An antiperspirant cream of the present invention is prepared as follows:

| Ingredient | Amount (weight percent) |
| --- | --- |
| cyclomethicone (D5) | 43.5 |
| dimethicone (350 cs) | 4.0 |
| Cab-O-Sil HS-5[1] | 4.0 |
| Microthene FN510[2] | 6.0 |
| Niacinamide | 0.5 |
| Tocopherol nicotinate | 0.5 |
| Glycerin | 0.1 |
| Natrosol[3] | 2.0 |
| iso-eicosane[4] | 13.0 |
| Reach AZ[5] | 26.7 |
| fragrance | 0.8 |

[1]Colloidal silica thickening material, sold by Cabot Corporation.-
[2]Low density polyethylene powder, sold by U.S.I. Chemicals.-
[3]Hydroxyethylcellulose, sold by Hercules. Inc.-
[4]2,2,4,4,6,6,8,8-dimethyl-10-methylundecane, obtained from Permethyl Corporation, Frazier, PA.-
[5]Zirconium-aluminum-glycine hydroxychloride complex, particulate antiperspirant active material, sold by Reheis Chemical Company.-

The cyclomethicone dimethicone, iso-cicosane and perfume are added to a stainless steel mixing vessel. The Cab-O-Sil is then added, followed by the Microthene and Natrosol and, finally, any remaining ingredients. The composition is thoroughly stirred after addition of each particulate material.

The composition is then milled, using a Black & Decker Die Grinder (Model 4420, type 4) with a 6.35 cm diameter Cowles dispersing blade at approximately 6,000 rpm, for approximately 5 minutes. The penetration force value of the milled composition is approximately 300 grams at 25° C., and 50% relative humidity.

An antiperspirant cream formulation, comprised as above, is applied to the underarm area of a human subject, and reduces the perspiration in the applied area and improves odor in this area.

Example IX

A waterproof mascara of the present invention is prepared as follows:

| Ingredient | Amount (weight percent) |
|---|---|
| Petroleum Distallate ((IBP 345) | 51.570 |
| Glycerol Ester of Tall Oil Rosin | 10.000 |
| Bentone 38 CG or Type | 5.890 (Gellant) |
| Color(Black 34-3068 or Type) | 5.000 |
| Alkylated PVP (220 Type) | 5.000 |
| Trihydroxystearin (R Type) | 5.000 (Gellant) |
| Magnesium Carbonate 309 | 5.000 (Filler) |
| Kaolin 2747 | 2.000 |
| Carnauba Wax, NF | 2.000 |
| Propylene Carbonate | 1.940 |
| Polyethylene AC-617A | 1.000 |
| Propylene Glycol | 1.000 |
| Niacinamide | 2.600 |
| Phenoxyethanol | 0.800 |
| Color (Yellow 34-3170 or Type) | 1.600 |
| Propylparaben, NF | 0.1000 |
| Tenox BHA | 0.100 |
| Total | 100.000 |

The above ingredients except colorants, niacinamide and gellants/fillers are added into stainless steel mixing vessel equipped with a heating source. The ingredients are heated to a temperature of about 90° C. and mixed using a propeller blade. Once the temperature reaches about 90° C., the ingredients are mixed using a dispersator blade at approximately 3500 rpm. The pigments are then slowly added during the mixing with the dispersator. Similarly, the niacinamide and gellants/fillers are added with mixing. The mixing is continued with the dispersator until the mixture is homogeneous. The mixture is then forced cooled while mixing with the dispersator at 3500 rpm. At about 40° C., mixing is discontinued and the mixture is transferred into an appropriate storage container.

The mascara composition is applied to the lashes and/or eyebrows to provide softening, moisturization and conditioning.

Example X

A mascara of the present invention is prepared as follows:

| Ingredient | Amount (weight percent) |
|---|---|
| Petroleum Distillate (IBP 345) | 49.570 |
| Glycerol Ester of Tall Oil Rosin | 10.000 |
| Bentone 38 CG or Type | 5.890 (Gellant) |
| Magnesium Carbonate 309 | 5.000 (Filler) |
| Alkylated PVP (220 Type) | 5.000 |
| Trihydroxystearin (R Type) | 5.000 (Gellant) |
| Talc 2755 | 4.790 (Filler) |
| Kaolin 2747 | 2.000 (Filler) |
| Carnauba Wax, NF | 2.000 |
| Propylene Carbonate | 1.940 |
| Propylene Glycol | 1.000 |
| Tocopherol nicotinate | 4.000 |
| Polyethylene AC-6 17A | 1.000 |
| Phenoxyethanol | 0.800 |
| Propylparaben, NF | 0.100 |
| Tenox BHA | 0.100 |
| Color(Blue 3403516 or Type) | 1.810 |
| Total | 100.000 |

The composition is prepared and used as in Example IX.

Example XI

A mascara of the present invention is prepared as follows:

| Petroleum Distillate (IBP 345) | 51.670 |
|---|---|
| Glycerol Ester of Tall Oil Rosin | 13.000 |
| Bentone 38 CG or Type | 5.890 (Gellant) |
| Magnesium Carbonate 309 | 5.000 (Filler) |
| Trihydroxystsearin (R Type) | 5.000 (Gellant) |
| Carnauba Wax, NF | 2.000 |
| Kaolin 2747 | 2.000 (Filler) |
| Propylene Carbonate | 1.940 |
| Glycerin | 1.000 |
| Niacinamide | 5.000 |
| Polyethylene AC-617A | 1.000 |
| Phenoxyethanol | 0.800 |
| Color | 5.500 |
| Tenox BHA | 0.100 |
| Propylparaben, NF | 0.100 |
| Total | 100.000 |

The composition is prepared and used as in Example IX.

Example XII

A lipstick of the present invention is prepared as follows:

| INGREDIENT | WT. %. |
|---|---|
| Polybutene | 4.536 |
| Lanolin Oil | 18.342 |
| Octoxyglyceryl Behenate | 18.342 |
| Stearyl heptanate | 8.856 |
| Jojoba oil | 8.856 |
| castor oil | 20.78 |
| Butylated hydroxytolueue | 0.054 |
| Butylated hydroxyanisole | 0.054 |
| Microcrystalline Wax | 6.84 |
| Polyethylene 500 | 6.84 |
| Association Structure Phase | |
| Lecithin | 0.475 |
| Glycerin | 1 |
| Niacinamide | 4.5 |
| Cholesterol | 0.475 |
| dicetyl phosphate | 0.05 |

In a suitable vessel, the castor oil, polybutene, lanolin oil, octoxyglyceryl behenate, stearyl heptanoate, jojoba oil, butylated hydroxytoluene, butylated hydroxyanisole, microcrystalline wax, polyethylene 500 are added to a vessel equipped with a heat source and heated to a temperature of from about 100–110° C. to form a melt. The melt is mixed until homogeneous. The niacinamide, lecithin, glycerin, cholesterol and dicetyl phosphate are mixed separately to form association structures. The association structure mixture is then added to the castor oil containing mixture and mixed until uniform. The mixture is deaerated by vacuum and poured into the appropriate mold. The mixture is cooled to ambient temperature and incorporated into the appropriate package.

The lipstick is applied to the lips to provide color, moisturization and improved lip feel.

Example XIII

A water-in-oil topical composition suitable for use as a liquid make-up foundation is prepared from the following ingredients using conventional mixing and formulating techniques such as described below.

| Ingredient | Wt. % |
|---|---|
| Part A | |
| cyclomethicone[1] | 15.15 |
| cetyl octanoate | 2.00 |
| dimethicone copolyol (DC5225C)[2] | 20.00 |
| Part B | |
| talc | 3.38 |
| pigment | 10.51 |
| Spheron L-1500[3] | 0.50 |
| Part C | |
| Synthetic Wax Durachem PT-0602[4] | 1.00 |
| Arachidyl behenate | 0.50 |
| Part D | |
| cyclomethicone[5] | 1.00 |
| trihydroxystearin | 0.30 |
| Part E | |
| laureth-7 | 0.50 |
| propyl paraben | 0.25 |
| Part G | |
| water | 17.44 |
| methyl paraben | 0.12 |
| propylene glycol | 2.00 |
| niacinamide | 20.00 |
| glycerin | 3.00 |
| sodium chloride | 2.00 |
| sodium dehydroacetate | 0.30 |
| fragrance | 0.05 |

[1]DC245 fluid supplied by Dow Corning
[2]Dimethicone copolyol (10%) and DC245 fluid (90%) supplied by Dow corning
[3]Sperical silica supplied by Presperse
[4]Synthetic wax supplied by Astor Wax Corp.
[5]DC245 fluid supplied by Dow Corning Combine the ingredients of parts A and B in a suitable container. Mix the ingredients using a Silverson L4RT mixer equipped w/ a 1" tubular assembly and a square hole screen for 30 minutes at 9000 rpm (the container can be covered to avoid loss of any volatile or other materials). Heat the resultant mixture to 85–90° C. Add ingredients C, mix for 5 minutes at 2100 rpm using a Silverson L4RT mixed equipped w/ a 2" head and a disintegrating screen. The container should be covered to minimize evaporation of cyclomethicone and other volatile or nonvolatile materials. Cool the resultant mixture to 45–55° C.

Combine the ingredients of part D and mix until a uniform slurry is formed. Separately, combine the ingredients E and mix until a uniform slurry is formed. Add the resultant slurries to the mixture of A, B and C (which is at 45–55° C.), mix for 5 minutes at 2100 rpm using a Silverson L4RT equipped w/ a 2" head and a disintegrating screen. Cool the resultant mixture to 30° C., then add ingredient fragrance. Mix 5 minutes at 2100 rpm using a Silverson L4RT equipped w/ a 2" head and a disintegrating screen.

Combine the ingredients of part G in a suitable container and mix. Slowly add the resultant solution to the mixture of A–G. Emulsify this combination using a Silverson L4RT mixer equipped w/a 2" head and a disintegrating screen at 2100–5100 rpm (rpms will increase as the mixture thickens), continue mixing for 5 minutes after all of the G mixture is added.

Apply the composition to a person's face once per day in an amount of 1–2 mg composition/cm$^2$ skin for four weeks, to observe a decrease in facial oil, a reduction in oily breakthrough, longer wear of the foundation, and more even coverage as the time period passes.

Other topical compositions suitable for use as a foundation are prepared in the above-described manner using pyridoxine, panthenol or pantothenic acid in place of niacinamide and are applied to the face as described above.

The foundation is applied to reduce fine lines and texture of skin as well as reduce oily shine.

Example XIV

A lipstick of the present invention is prepared as follows:

| INGREDIENT | W/W % |
|---|---|
| Octyl Palmitate | 11.24 |
| Isopropyl Palmitate | 4.80 |
| Bentone 38[1] | 1.00 |
| Propylene Carbonate | 0.33 |
| Cetyl Recinolate | 1.00 |
| Diisopropyl Dimearate | 6.12 |
| Lanolin Oil | 11.60 |
| Ozokerite | 6.75 |
| Candelilla | 5.25 |
| Be Square 175[2] | 2.00 |
| Granulated Lecithin | 2.00 |
| PG-3 Diisostearate | 0.83 |
| Vitamin "E" Acetate | 0.05 |
| Propylparaben | 0.15 |
| Methylparaben | 0.15 |
| Benzoic Acid | 0.10 |
| Glycerine | 6.00 |
| Mica cf[3] | 7.00 |
| Niacinamide | 5.00 |
| Pigment (35%) slurried in Diisopropyl Dimerate | 25.31 |
| Stainers | 2.92 |

[1]Quaternium-18 hectorite, supplied by Rheox
[2]Microcrystalline wax, supplied by Petrolite
[3]Non-treated mica, Mearlmica MMCF, supplied by Mearl In a suitable vessel equipped with a heat source, the cetyl recinolate, diisopropyl dimerate, lanolin oil, ozokerite, candelilla, Be Square 175, granulated lecithin, PG-3 diisostearate, vitamin E acetate, propylparaben, methylparaben, benzoic acid, glycerine. Mica cf, niacinamide are added and heated to a temperature of from about 80–90° C. to form a melt. The melt is mixed until homogeneous.

In a separate container, the octyl palmitate, isopropyl palmitate, Bentone 38 and propylene carbonate are mixed to form a gel. The gel, pigment slurry and stainers are added to the niacinamide melt and mixed until homogeneous. The mixture is deaerated by vacuum and poured into the appropriate mold. The mixture is cooled to ambient temperature and incorporated into the appropriate package.

The lipstick is applied to the lips to provide color, moisturization and improved lip feel.

Example XV

A lipstick of the present invention is prepared as follows:

| Ingredient | % W/W |
|---|---|
| Isopropyl Isostearate | 12.58 |
| Octyl Palmitate | 8.55 |
| Isopropyl palmitate | 5.27 |
| Ozokerite Wax | 5.00 |
| Candelilla Wax | 3.00 |
| Paraffin Wax | 3.00 |

-continued

| Ingredient | % W/W |
|---|---|
| Caranauba Wax | 2.00 |
| Cetyl Alcohol | 2.00 |
| Cetyl Lactate | 2.00 |
| Ascorbyl Palmitate | 0.50 |
| Propyl paraben | 0.10 |
| Vitamin E Acetate | 0.05 |
| Octyl Methoxycinnimate | 7.25 |
| Micronized TiO$_2$ in castor oil (25% slurry) | 8.00 |
| Niacinamide | 5.00 |
| Glycerin | 0.10 |
| Mica SVA[1] | 10.00 |
| Pigment (35% slurried in Diisopropyl Dimerate | 25.60 |

[1]Lauroyl lysine treated mica, Mearlmica SVA, supplied by Mearl

The micronized TiO$_2$ in castor oil are ball milled to the desired particle size. Similarly, the pigments in diisopropyl dimerate are ball milled to the desired particle size. Next, the TiO$_2$ and pigments are combined with the remaining ingredients in a vessel equipped with a heat source. The mixture is heated to a temperature of from about 85–90° C. to form a melt. The melt is mixed until homogeneous. The mixture is deaerated by vacuum and poured into the appropriate mold. The mixture is cooled to ambient temperature and incorporated into the appropriate package.

The lipstick is applied to the lips to provide color, moisturization and improved lip feel.

Example XVI

A lipstick of the present invention is prepared as follows:

| Ingredient | % W/W |
|---|---|
| Isopropyl Isostearate | 12.58 |
| Octyl Palmitate | 8.55 |
| Isopropyl palmitate | 5.27 |
| Ozokerite Wax | 5.00 |
| Candelilla Wax | 3.00 |
| Paraffin Wax | 3.00 |
| Caranauba Wax | 2.00 |
| Cetyl Alcohol | 2.00 |
| Cetyl Lactate | 2.00 |
| Ascorbyl Palmitate | 0.50 |
| Propylparaben | 0.10 |
| Vitamin E Acetate | 0.05 |
| Octyl Methoxycinnimate | 7.25 |
| Micronized TiO2 in castor oil (25% slurry) | 8.00 |
| Niacinamide | 5.00 |
| Glycerin | 0.10 |
| Mica SVA[1] | 10.00 |
| Pigment (35%) slurried in Diisopropyl Dimerate | 25.60 |
| Lecithin | 0.05 |

[1]Lauroyl lysine treated mica, Mearlmica SVA, supplied by Mearl

The micronized TiO$_2$ in castor oil are ball milled to the desired particle size. Similarly, the pigments in diisopropyl dimerate are ball milled to the desired particle size. Next, the TiO$_2$ and pigments are combined with the remaining ingredients except lecithin in a vessel equipped with a heat source. The mixture is heated to a temperature of from about 85–90° C. to form a melt. The melt is mixed until homogeneous. The lecithin is then added with mixing until homogeneous. The mixture is deaerated by vacuum and poured into the appropriate mold. The mixture is cooled to ambient temperature and incorporated into the appropriate package.

The lipstick is applied to the lips to provide color, moisturization and improved lip feel.

Example XVII

The following steps describe the preparation of a long lasting cosmetic emulsion composition.

A. An admixture (Part A) is prepared by combining in a suitable vessel the following ingredients:

| INGREDIENT | WT. %. |
|---|---|
| MQ Resin[1] | 43.7 |
| PM99A[2] | 56.3 |

[1]Trimethylsiloxysilicate available from GE.
[2]Isododecane available from Presperse.

The admixture is mixed using conventional mixing techniques until the MQ Resin is dissolved. Processing:

B. An admixture (Part B) is prepared by combining in a suitable vessel the following ingredients:

| INGREDIENT | WT. %. |
|---|---|
| SE30 Silicone Gum[1] | 50.0 |
| PM99A | 50.0 |

[1]Available from GE.

The admixture is mixed using conventional mixing techniques until the SE30 Silicone Gum is dissolved.

C. A cosmetic emulsion composition containing Part A and Part B is prepared by combining the following ingredients:

| INGREDIENTS | WT. Gms. |
|---|---|
| Part A | 38.67 |
| Part B | 20.78 |
| Pigments | 10.00 |
| PM99A | 1.41 |
| Propylparaben | 0.20 |
| Bentone ISD | 15.00 |
| Water | 6.00 |
| Niacinamide | 7.00 |
| Laponite XLS[1] | 0.94 |

[1]Hydrous sodium lithium magnesium silicate available from Southern Clay Products In a suitable vessel, the admixture of Part A along with the pigments, propylparaben and PM99A are combined and mixed using a Ultra Turrax T25 homogenizer at about 8,000 rpms. for about 10 minutes or until the cosmetic mixture is uniform (taking care not to ignite the PM99A). The Bentone ISD added to the mixture with mixing at about 8,000 rpms. until the mixture is uniform. The Laponite XLS, water, and niacinamide are mixed together in a separate vessel and then added to the cosmetic mixture with mixing using a Ross homogenizer at about 3,500 rpms until uniform. The admixture of Part B is added to the cosmetic mixture and mixed initially at high shear, preferably 1600 rpms., to facilitate dispersion using an IKA mixer. Once sufficient dispersion is achieved, the mixer speed is reduced, preferably to about 1,000 rpms., and the cosmetic mixture is allowed to mix until uniform. The cosmetic mixture is then poured into a suitable container and tightly capped for storage, preferably at room temperature.

The cosmetic emulsion composition is applied to impart color to the skin, improve skin texture and skin feel.

What is claimed is:

1. A method of improving the skin penetration of vitamin $B_3$ compounds by applying to the skin a safe and effective amount of a cosmetic composition, said composition comprising:
   a) from about 0.01% to about 50%, by weight, of a vitamin $B_3$ compound;
   b) from about 0% to about 90%, by weight, of an emollient component comprising from 0% to about 100%, by weight, of an oil liquid at ambient temperature;
   c) from about 0.01% to about 80%, by weight, of a polar solvent;
   d) from about 0% to about 30%, by weight, of a surfactant;
   e) from about 0% to about 90%, by weight, of a solidifying agent; and
   f) from about 0% to about 90%, on an anhydrous basis, of a color wherein the vitamin $B_3$ compound is added to the composition such that the concentration of the vitamin $B_3$ compound exceeds the saturation solubility of the vitamin $B_3$ compound in the composition.

2. A method of preparing cosmetic compositions, comprising the steps of:
   a.) providing a polar solvent;
   b.) dissolving a vitamin $B_3$ compound in the polar solvent at an amount greater than the saturation solubility at ambient temperature of the vitamin $B_3$ compound in the polar solvent such that undissolved vitamin $B_3$ compound is present; and
   c.) combining the admixture of step b.) with a dermatologically acceptable cosmetic carrier.

3. A method of improving the skin penetration of vitamin $B_3$ compounds by applying to the skin a safe and effective amount of a cosmetic composition, said composition comprising:
   a) from about 0.01% to about 50%, by weight, of a vitamin $B_3$ compound;
   b) from about 0% to about 90%, by weight, of an emollient component comprising from 0% to about 100%, by weight, of an oil liquid at ambient temperature;
   c) from about 0.01% to about 80%, by weight, of a polar solvent;
   d) from about 0% to about 30%, by weight, of a surfactant;
   e) from about 0% to about 90%, by weight, of a solidifying agent; and
   f) from about 0% to about 90%, on an anhydrous basis, of a color wherein the vitamin $B_3$ compound is added to the composition such that the concentration of the vitamin $B_3$ compound will be at least about 50% greater than the saturation solubility of the vitamin $B_3$ compound in the composition at ambient temperature.

4. A method according to claim 1, wherein the concentration of the vitamin $B_3$ compound will be at least about 100% greater than the saturation solubility of the vitamin $B_3$ compound in the composition at ambient temperature.

5. A method according to claim 1, wherein the concentration of the vitamin $B_3$ compound will be at least about 150% greater than the saturation solubility of the vitamin $B_3$ compound in the composition at ambient temperature.

6. A method according to claim 1, wherein said vitamin $B_3$ compound is selected from niacinamide, derivatives of niacinamide, non-vasodilating esters of nicotinic acid, and combinations thereof.

7. A method according to claim 1, wherein said vitamin $B_3$ compound is selected from niacinamide, tocopherol nicotinate, and combinations thereof.

8. A method according to claim 7, wherein said vitamin $B_3$ compound is niacinamide.

9. A method according to claim 1, wherein said vitamin $B_3$ compound is substantially free of salts of the vitamin $B_3$ compound.

10. A method according to claim 1, wherein said vitamin $B_3$ compound is substantially uncomplexed.

11. A method according to claim 1, wherein said surfactant forms association structures and is selected from the group consisting of amphoteric surfactants, anionic surfactants, cationic surfactants, nonionic surfactants and mixtures thereof.

12. A method according to claim 11, wherein said association structure is selected from the group consisting of cylindrical micelles, lyotropic liquid crystals and mixtures thereof.

13. A method according to claim 12, wherein said association structure is selected from the group consisting of unilamellar vesicles, multilamellar vesicles, cylindrical reverse micelles, hexagonal liquid crystals, cubic liquid crystals, lamellar liquid crystals and mixtures thereof.

14. A method according to claim 13, wherein said association structure is selected from the group consisting of lamellar liquid crystals, hexagonal liquid crystals and mixtures thereof.

15. A method according to claim 14, wherein said micelles aggregate to form networking spherical structures, elongated structures, cylindrical structures, filament structures, or mixtures thereof.

16. A method according to claim 14, wherein said lamellar liquid crystals are substantially one phase.

17. A method according to claim 11, wherein said association structure comprises from about 0.1% to about 75% of the cosmetic composition.

18. A method according to claim 17, wherein said association structure comprises from about 10% to about 65% of the cosmetic composition.

19. A method according to claim 1, wherein said surfactant forms an oil-in-water or water-in-oil emulsion.

20. A method according to claim 1, wherein said polar solvent is selected from the group consisting of water, glycerine, propylene glycol, butylene glycol, hexylene glycol, alcohol, panthenol and mixtures thereof.

* * * * *

UNITED STATES PATENT AND TRADEMARK OFFICE
CERTIFICATE OF CORRECTION

PATENT NO.    : 6,224,888 B1
DATED         : May 1, 2001
INVENTOR(S)   : M. L. Vatter et al.

It is certified that error appears in the above-identified patent and that said Letters Patent is hereby corrected as shown below:

Column 1,
Line 37, after the word "comprising", insert the text -- which enhance the amount of topically applied vitamin B3 compounds which penetrate the skin.
Another aspect of the present invention is to provide cosmetic compositions --.

Column 2,
Line 19, "foundations" should read -- foundation --.

Column 6,
Lines 19-20, "lipstick" should read -- lipsticks --.
Line 27, "hyroxystearate" should read -- hydroxystearate --.
Line 40, "polyglyerol" should read -- polyglycerol --.

Column 7,
Line 15, "temperature" should read -- temperate --.

Column 8,
Line 43, after the word "among", insert the text
-- the preferred high-melting point waxes useful herein. Compositions containing waxes among --.

Column 9,
Line 17, "and" should read -- are --.
Line 35, after the word "higher", delete "acid".

Column 11,
Line 61, "it" should read -- in --.

Column 12,
Line 58, "or" should read -- of --.

Column 13,
Line 45, "conventional" should read -- convenient --.

UNITED STATES PATENT AND TRADEMARK OFFICE
CERTIFICATE OF CORRECTION

PATENT NO. : 6,224,888 B1
DATED : May 1, 2001
INVENTOR(S) : M. L. Vatter et al.

It is certified that error appears in the above-identified patent and that said Letters Patent is hereby corrected as shown below:

Column 14,
Line 48, "its" should read -- their --.

Column 15,
Line 58, "mixed," should read -- mixed --.

Column 16,
Line 44, "Polysiloxane Copolymer[1]" should read -- Polysiloxane Copolymer[1] 5.97 --.

Column 21,
Line 43, "mixed" should read -- mixer --.

Column 22,
Line 38, "dimerate" should read -- dimearate --.

Signed and Sealed this

Eighteenth Day of February, 2003

JAMES E. ROGAN
*Director of the United States Patent and Trademark Office*